(12) United States Patent
Wang et al.

(10) Patent No.: US 8,340,384 B2
(45) Date of Patent: Dec. 25, 2012

(54) METHOD AND APPARATUS FOR CEREBRAL HEMORRHAGE SEGMENTATION

(75) Inventors: Xueli Wang, Beijing (CN); Qi Zhao, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 855 days.

(21) Appl. No.: 12/304,431

(22) PCT Filed: Jun. 13, 2006

(86) PCT No.: PCT/CN2006/001314
§ 371 (c)(1),
(2), (4) Date: Jun. 23, 2009

(87) PCT Pub. No.: WO2008/006238
PCT Pub. Date: Jan. 17, 2008

(65) Prior Publication Data
US 2010/0040271 A1    Feb. 18, 2010

(51) Int. Cl.
*G06K 9/00* (2006.01)
(52) U.S. Cl. ........................................ 382/131; 600/407
(58) Field of Classification Search .................. 382/131; 600/407
See application file for complete search history.

(56) References Cited

U.S. PATENT DOCUMENTS

| | | | |
|---|---|---|---|
| 6,138,045 A | 10/2000 | Kupinski et al. | |
| 6,875,175 B2 | 4/2005 | Luce | |
| 6,891,922 B2 | 5/2005 | Ferrant et al. | |
| 7,684,600 B2 * | 3/2010 | Wang | 382/128 |
| 7,792,339 B2 * | 9/2010 | Li | 382/128 |
| 2002/0095087 A1 | 7/2002 | Mourad et al. | |
| 2003/0018244 A1 | 1/2003 | Haddad et al. | |
| 2006/0079773 A1 | 4/2006 | Mourad et al. | |
| 2007/0031020 A1 | 2/2007 | Li | |
| 2007/0167746 A1 | 7/2007 | Wang | |

FOREIGN PATENT DOCUMENTS

| | | |
|---|---|---|
| CN | 1547161 A | 11/2004 |
| CN | 1781456 A | 6/2006 |
| JP | 2005-118510 | 5/2005 |

OTHER PUBLICATIONS

Loncaric et al., "3-D image analysis of intra-cerebral brain hemorrhage from digitized CT films", 1995, Computer Methods and Programs in Biomedicine 46 (1995) 207-216.*

(Continued)

*Primary Examiner* — Chan S Park
*Assistant Examiner* — Katrina Fujita
(74) *Attorney, Agent, or Firm* — Armstrong Teasdale LLP

(57) ABSTRACT

An apparatus for segmenting a cerebral hemorrhage site in a medical image of a head comprises a means for segmenting an internal region of a skull bone in the medical image of the head, a means for segmenting a possible region in which a cerebral hemorrhage site is contained, out of the region segmented by the means for segmenting the internal region of the skull bone, and a means for determining a cerebral hemorrhage site out of the region segmented by the means for segmenting the possible region in which the cerebral hemorrhage site is contained.

16 Claims, 18 Drawing Sheets

OTHER PUBLICATIONS

Loncaric et al., "Quantitative intracerebral brain hemorrhage analysis", 1999, Proceedings vol. 3661 Medical Imaging 1999: Image Processing, pp. 886-894.*

Strik et al., "Three-dimensional reconstruction and volumetry of intracranial haemorrhage and its mass effect" 2005, Neuroradiology (2005) 47: 417-424.*

Shang, et al.; A Method of CT Image Segmentation in Stroke Patients; Computer Engineering; Dec. 2004; 3 pages; Supplementary Issue vol. 30.

Office Action dated Jun. 17, 2010; CN Patent Application No. 200680054972; 5 pages.

Office Action dated Jun. 17, 2010; (English Translation of CN Patent Application No. 200680054972); 6 pages.

* cited by examiner

P1

P2

P3

P5

P7

US 8,340,384 B2

METHOD AND APPARATUS FOR CEREBRAL HEMORRHAGE SEGMENTATION

CROSS REFERENCE TO RELATED APPLICATIONS

This application claims the benefit of PCT/CN2006/001314 filed Jun. 13, 2006, which is hereby incorporated by reference in its entirety.

BACKGROUND OF THE INVENTION

The embodiments described herein relate relates to a method and apparatus for cerebral hemorrhage segmentation, more specifically to a method and apparatus for identifying the cerebral hemorrhage based on an X-ray CT image of the head having the cerebral hemorrhage onset.

The cerebral hemorrhage is segmented on the head X-ray CT image for the diagnosis and treatment of the cerebral hemorrhage. The segmentation is manually conducted by the intervention of a specialist (for example, see Japanese Patent Application No. 2005-118510).

BRIEF DESCRIPTION OF THE INVENTION

Manual segmentation by the intervention of a specialist takes time and labor. In addition the result of the segmentation is depending on the skill of the physician. The automation of the segmentation by a single threshold may not solve the problem because the CT value at the cerebral hemorrhage may vary in relation to the symptom, and may overlap to the CT values of healthy part.

An object of the present invention is to provide a method and apparatus for appropriate segmentation of cerebral hemorrhage lesion.

DETAILED DESCRIPTION OF THE INVENTION

Figure 1:
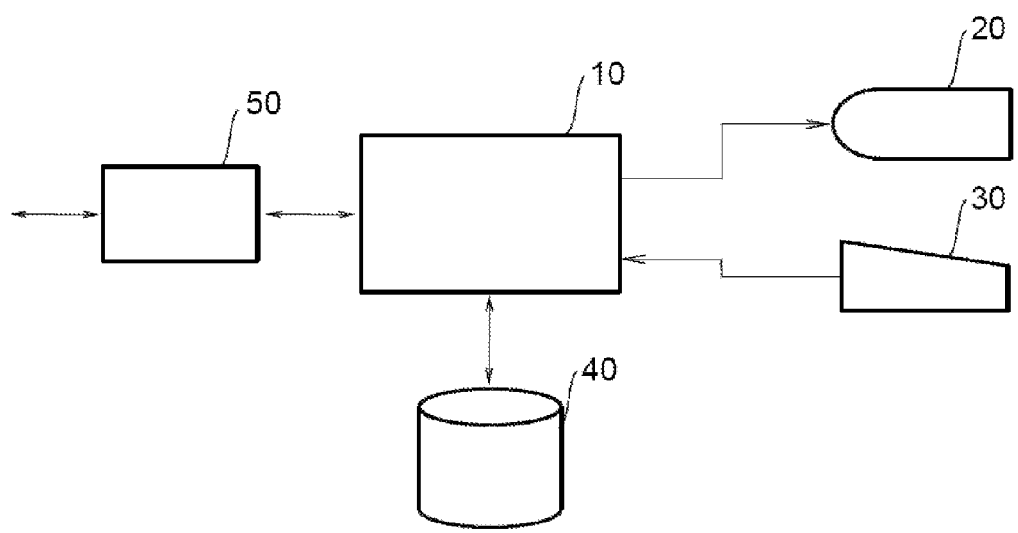
FIG. 1 is a schematic block diagram of an exemplary image processing apparatus.

A first aspect provides a method of segmenting a cerebral hemorrhage site in a medical image of a head. The method includes segmenting an internal region of a skull bone in the medical image of said head, segmenting a possible region in which a cerebral hemorrhage site is contained, out of a region segmented in said step of segmenting the internal region of the skull bone, and determining a cerebral hemorrhage site out of a region segmented in said step of segmenting the possible region in which the cerebral hemorrhage site is contained.

In some embodiments, the step of segmenting a possible region in which a cerebral hemorrhage site is contained includes segmenting a region with CT values gradually changing out of the region segmented in said step of segmenting the internal region of the skull bone, segmenting a region with the number of pixels larger than a predetermined number, out of the region segmented in said step of segmenting a region with CT values gradually changing, segmenting a region with a comparatively large CT value out of the region segmented in said step of segmenting a region with the number of pixels larger than a predetermined number, and segmenting a region with CT values gradually changing out of the region segmented in said step of segmenting a region with a comparatively large CT value.

In some embodiments, the step of determining a cerebral hemorrhage site includes, for the region segmented in the step of segmenting the possible region in which the cerebral hemorrhage site is contained, a first step of determining whether or not the segmented region is a cerebral hemorrhage site based on a CT value and a size of the segmented region, and for a potential region of the cerebral hemorrhage site out of a region other than the region which has been determined as the cerebral hemorrhage site in the first step, a second step of determining whether or not the potential region is the cerebral hemorrhage site based on a CT value difference between the potential region and a vicinity thereof or a CT value of the region.

In some embodiments, the method further includes correcting the influence of a partial volume effect for the region which has been determined as the cerebral hemorrhage site in said step of determining a cerebral hemorrhage site.

More specifically, a method for cerebral hemorrhage segmentation includes the steps of preprocessing, primary searching, analyzing and adjusting, filtering, secondary searching, analyzing and determining, and postprocessing. The preprocessing step, on the X-ray CT image of the head, excludes pixels having a CT value larger than a first setting value and pixels having a CT value less than a second setting value, identifying the boundary of the skull bone based on a third setting value, and excludes the outer region of the skull bone based on the boundary identified. The primary searching step, on the image that has been processed by the preprocessing, searches the region where the CT value varies gradually, and labels each region found by the searching; the analyzing and adjusting step determines, on the image on which the first searching has been performed, the number of pixels for each of the regions and excludes the region having the number of pixels less than a fourth setting value. The filtering step determines, on the image on which the analyzing and adjusting step has been performed, the sum of the absolute value of the difference of the CT value pixel by pixel between adjacent two pixels in the direction that a two-dimensional coordinates i, j is increasing, for each of the regions, identifies the pixel position that the sum is more than a fifth setting value, determines the mean value of CT values at all of the pixel positions identified, and excludes the pixels having a CT value equal to or less than the mean value. The secondary searching step searches, on the image on which the filtering has been performed, a region where the CT value gradually changes, and newly labels each region found by the searching. The analyzing and determining step sets, on the image that has been searched by the second searching, a first index $Index_{CT}$ to $$Index_{CT}=(CT_{Region}-CT_{min})/(CT_{blood}-CT_{Min}) \qquad \text{Eq. (1)}$$

if $CT_{min}<=CT_{Region}<=CT_{Blood}$,
where $CT_{Region}$ is the CT value of the pixel in the region, $CT_{max}$ is sixth setting value, $CT_{min}$ is seventh setting value, and $CT_{Blood}$ is eighth setting value. Alternatively, the analyzing and determining step sets $$Index_{CT}=(CT_{max}-CT_{region})/(CT_{max}-CT_{blood}) \qquad \text{Eq. (2)}$$

if $CT_{Blood}<CT_{Region}<=CT_{max}$ or else sets to $Index_{CT}=0$;
when the surface area and the perimeter length of the region are indicated as Area and Perimeter, and the characteristics value of the region is indicated by $$Radian=Area/Perimeter^2 \qquad \text{Eq. (3)}$$

then a second index $Index_{Radian}$ is set to
$Index_{Radian}=1$ if Radian is more than a ninth setting value $Radian_{max}$,
$Index_{Radian}=0$ if Radian is less than a tenth setting value $Radian_{min}$, and to $$Index_{radian}=(Radian_{region}-Radian_{Min})/(Radian_{max}-Radian_{Min}) \qquad \text{Eq. (4)}$$

if Radian is less than or equal to the ninth setting value $Radian_{max}$ and more than or equal to the tenth setting value $Radian_{min}$ sets a third index $index_0$ to Equation 24

$$Index_0=Index_{CT}*Index_{radian}, \qquad \text{Eq. (5)}$$

then determines that the regions has the cerebral hemorrhage if $index_0>=20\%$, or that the region has not the cerebral hemorrhage if $Index_0<=3\%$, or, if $3\%<Index_0<20\%$,
$CT_{AroundRegion}$ is the CT value of the pixel of the surrounding region of the region, and $CT_{Average-All-Region}$ is the mean CT value of all regions, then sets a fourth index $Index_{sub}$ to $$Index_{sub}=CT_{Region}-CT_{AroundRegion}, \qquad \text{Eq. (6)}$$

and a fifth index $Index_{Order}$ to $$Index_{Order}=CT_{Region}-CT_{Average-All-Region}, \qquad \text{Eq. (7)}$$

and determines that the region has a cerebral hemorrhage if $Index_{sub}>=8$ or $Index_{Order}>=10$,
or determines that the region has not a cerebral hemorrhage if $Index_{sub}<=0$ or $Index_{Order}<=-5$,
or, if $0<Index_{sub}<8$ and $-5<Index_{Order}<10$, then set a sixth index $Index_{Final}$ to $$Index_{Final}=Index_0*(Index_{Order}-(-5))/(10-(-5)) \qquad \text{Eq. (8)}$$

and determines that the region has a cerebral hemorrhage if $Index_{Final}>=50\%$,
or determines that the region has not a cerebral hemorrhage if $Index_{Final}<50\%$;
and the postprocessing step compensates for the influence of partial volume effect on the region determined as having a cerebral hemorrhage in the analyzing and determining step.

A second aspect provides an apparatus for segmenting a cerebral hemorrhage site in a medical image of a head. The apparatus includes a means for segmenting an internal region of a skull bone in the X-ray CT image of said head, a means for segmenting a possible region in which a cerebral hemorrhage site is contained, out of a region segmented by said means for segmenting the internal region of the skull bone, and a means for determining a cerebral hemorrhage site out of a region segmented by said means for segmenting a possible region in which a cerebral hemorrhage site is contained.

In some embodiments, the means for segmenting a possible region in which a cerebral hemorrhage site is contained includes a means for segmenting a region with CT values gradually changing out of the region segmented by said means for segmenting the internal region of the skull bone, a means for segmenting a region with the number of pixels larger than a predetermined number, out of the region segmented by said means for segmenting a region with CT values gradually changing, a means for segmenting extracting a region with comparatively large CT value out of the region segmented by said means for segmenting a region with the number of pixels larger than a predetermined number, and a means for segmenting a region with CT values gradually changing out of the region segmented in said step of segmenting a region with comparatively large CT value.

In some embodiments, the means for determining a cerebral hemorrhage site includes, for the region segmented by said means for segmenting the possible region in which the cerebral hemorrhage site is contained, a first means for determining whether or not said segmented region is a cerebral hemorrhage site based on a CT value and a size of said segmented region, and for a potential region of the cerebral hemorrhage site out of a region other than the region which has been determined as the cerebral hemorrhage site by said first means, a second means for determining whether or not said potential region is the cerebral hemorrhage site based on a CT value difference between said potential region and a vicinity thereof or a CT value of said region.

In some embodiments, the apparatus further includes a means for correcting the influence of a partial volume effect for the region which has been determined as the cerebral hemorrhage site by said means for determining a cerebral hemorrhage site.

More specifically, an apparatus for segmentation of a cerebral hemorrhage region on an X-ray CT image of a head, includes a preprocessing means, a primary searching means, an analyzing and adjusting means, a filtering means, a secondary searching means, an analyzing and determining means, and a postprocessing means. The preprocessing means, on the X-ray CT image of the head, excludes pixels having a CT value larger than a first setting value and pixels having a CT value less than a second setting value, identifies the boundary of the skull bone based on a third setting value, and excludes the outer region of the skull bone based on the boundary identified. The primary searching means, on the image that has been preprocessed by the preprocessing, searches the region where the CT value gradually changes, and labels each region found by the searching. The analyzing and adjusting means, on the image that has been searched by the primary searching, determines the number of pixels for each of the regions, and excludes the region having the number of pixels less than a fourth setting value. The filtering means, on the image that has been analyzed and adjusted, for each of the regions, determines the sum of the absolute value of the difference of the CT value between adjacent pixels for each pixel in the direction wherein a two-dimensional coordinate i, j is increasing, identifies the pixel position that the sum is more than a fifth setting value, determines the mean value of CT values at all of the pixel positions identified, and excludes the pixels having a CT value less than the mean value. The secondary searching means, on the image that has been filtered by the filtering, searches a region where the CT value gradually changes, and newly labels each region found by the searching. The analyzing and determining means, on the image that has been searched by the secondary searching, sets a first index $Index_{CT}$ to $$Index_{CT}=(CT_{Region}-CT_{min})/(CT_{blood}-CT_{Min}) \qquad \text{Eq. (1)}$$

if $CT_{min}<=CT_{Region}<=CT_{Blood}$, or sets to $$Index_{CT}=(CT_{max}-CT_{region})/(CT_{max}-CT_{blood}) \qquad \text{Eq. (2)}$$

if $CT_{Blood}<CT_{Region}<=CT_{max}$, or sets to
Equation 30
$Index_{CT}=0$,
where $CT_{Region}$ is the CT value of the pixel in the region,
$CT_{max}$ is a sixth setting value,
$CT_{min}$ is a seventh setting value, and
$CT_{Blood}$ is an eighth setting value;
when the surface area and the perimeter length of the region are indicated as Area and Perimeter, and the characteristics value of the region is indicated by $$Radian=Area/Perimeter2 \qquad \text{Eq. (3)}$$

then sets a second index $Index_{Radian}$ to
$Index_{Radian}=1$ if Radian is more than a ninth setting value $Radian_{max}$,
$Index_{Radian}=0$ if Radian is less than a tenth setting value $Radian_{min}$, and to $$Index_{radian}=(Radian_{region}-Radian_{Min})/(Radian_{max}-Radian_{Min}) \qquad \text{Eq. (4)}$$

if Radian is less than or equal to the ninth setting value $Radian_{max}$ and more than or equal to the tenth setting value $Radian_{min}$, sets a third index $index_0$ to $$Index_0=Index_{CT}*Index_{Radian} \qquad \text{Eq. (5)}$$

then determines that the regions has the cerebral hemorrhage if $index_0>=20\%$,
or determines that the region has not the cerebral hemorrhage if $index_0<=3\%$,
or if $3\%<index_0<20\%$, and when $CT_{AroundRegion}$ is the CT value of the pixel of the surrounding region of the region, and $CT_{Average-All-Region}$ is the mean CT value of all regions, then sets a fourth index $Index_{sub}$ to $$Index_{Sub}=CT_{Region}-CT_{AroundRegion} \qquad \text{Eq. (6)}$$

and a fifth index $Index_{Order}$ to $$Index_{Order}=CT_{Region}-CT_{Average-All-Region} \qquad \text{Eq. (7)}$$

and determines that the region has a cerebral hemorrhage if $Index_{Sub}>=8$ or $Index_{Order}>=10$,
or determines that the region has not a cerebral hemorrhage if $Index_{Sub}<=0$ or $Index_{Order}<=-5$,
or, if $0<Index_{Sub}<8$ and $-5<Index_{Order}<10$, then set a sixth index $Index_{Final}$ to $$Index_{Final}=Index_0*(Index_{Order}-(-5))/(10-(-5)) \qquad \text{Eq. (8)}$$

and determines that the region has a cerebral hemorrhage if $Index_{Final}>=50\%$,
or determines that the region has not a cerebral hemorrhage if $Index_{Final}<50\%$;
the postprocessing means compensates for the influence of partial volume effect on the region determined as having a cerebral hemorrhage in the analyzing and determining.

The identification of the skull boundary in the preprocessing is preferably performed by detecting the CT value changing point from a value smaller than the third setting value to a larger value, or the CT value changing point from a value larger than the third setting value to a smaller value, in order to appropriately identify the boundary.

The region search in the primary searching and the second searching is preferably performed by searching a region that has the difference of CT value between adjacent two pixels of 5 or less, in order to appropriately search a region.

The compensation in the postprocessing is preferably performed by a dilation calculation with respect to the region in order to appropriately compensate for a region.

Preferably the first setting value is 245, the second setting value is 30, the third setting value is 190, the fourth setting value is 300, the fifth setting value is 4, the sixth setting value is 100, the seventh setting value is 40, the eighth setting value is 70, the ninth setting value is 0.015, and the tenth setting value is 0.003 in order to perform a segmentation in a high precision.

In accordance with the above aspects of the present invention, the index $Index_{CT}$ with respect to the CT value of the pixels in a candidate region and the index $Index_{Radian}$ with respect to the characteristics of the candidate region are used to generate the index $Index_0$, the region of interest is determined to have a cerebral hemorrhage if $Index_0>=20\%$, or the region is determined not to have a cerebral hemorrhage if $Index_0<=3\%$. If $3\%<Index_0<20\%$ then the $Index_{sub}$ and $Index_{Order}$ are generated for the region, then the region is determined to have a cerebral hemorrhage if $Index_{sub}>=8$ or $Index_{Order}>=10$, or the region is determined not to have a cerebral hemorrhage if $Index_{sub}<=0$ or $Index_{Order}<=-5$. If $0<Index_{sub}<8$ and $-5<Index_{Order}<10$, an index $Index_{Final}$ generated to determine that the region has a cerebral hemorrhage if $Index_{Final}>=50\%$, or that the region has not a cerebral hemorrhage if $Index_{Final}<50\%$. In this manner a method and apparatus for appropriately performing the cerebral hemorrhage segmentation is achieved.

Embodiments of the present invention will be described in greater details with reference to the accompanying drawings. It should be noted here that the present invention is not limited to the embodiments described herein. Now referring to the drawings, FIG. 1 shows a schematic block diagram of an image processing apparatus.

As shown in FIG. 1, the apparatus includes a data processing unit 10, a display unit 20, an operation console 30, a storage unit 40, and an input and output unit 50. The data processing unit 10 performs a predetermined data processing on the data stored in the storage unit 40 based on the interactive operation by a user through the display unit 20 and the operation console 30.

The data processing unit 10 also performs data input and output through the input and output unit 50 to an external device. The X-ray CT images to be subject of the cerebral hemorrhage segmentation will be input through the input and output unit 50.

Figure 2:
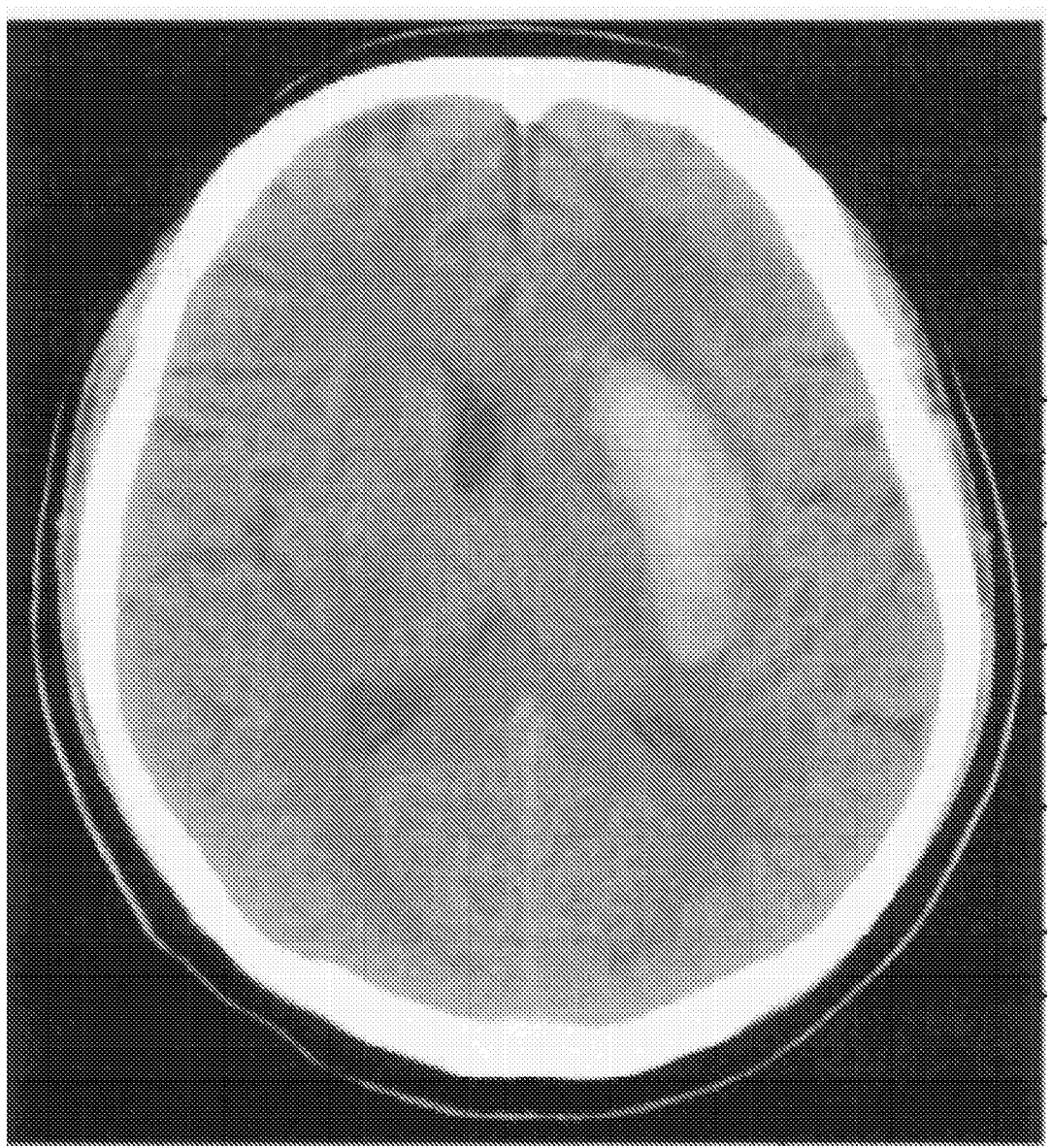
FIG. 2 is a schematic diagram illustrating an exemplary X-ray CT image as gray-scale photograph.

Some typical examples of the external devices include an X-ray CT apparatus and a medical image server. The apparatus may also be part of an X-ray CT apparatus or a medical image server. In the latter case the input and output unit 50 is not necessarily required. FIG. 2 shows an example of X-ray CT image to be subject of the cerebral hemorrhage segmentation.

Figure 3:
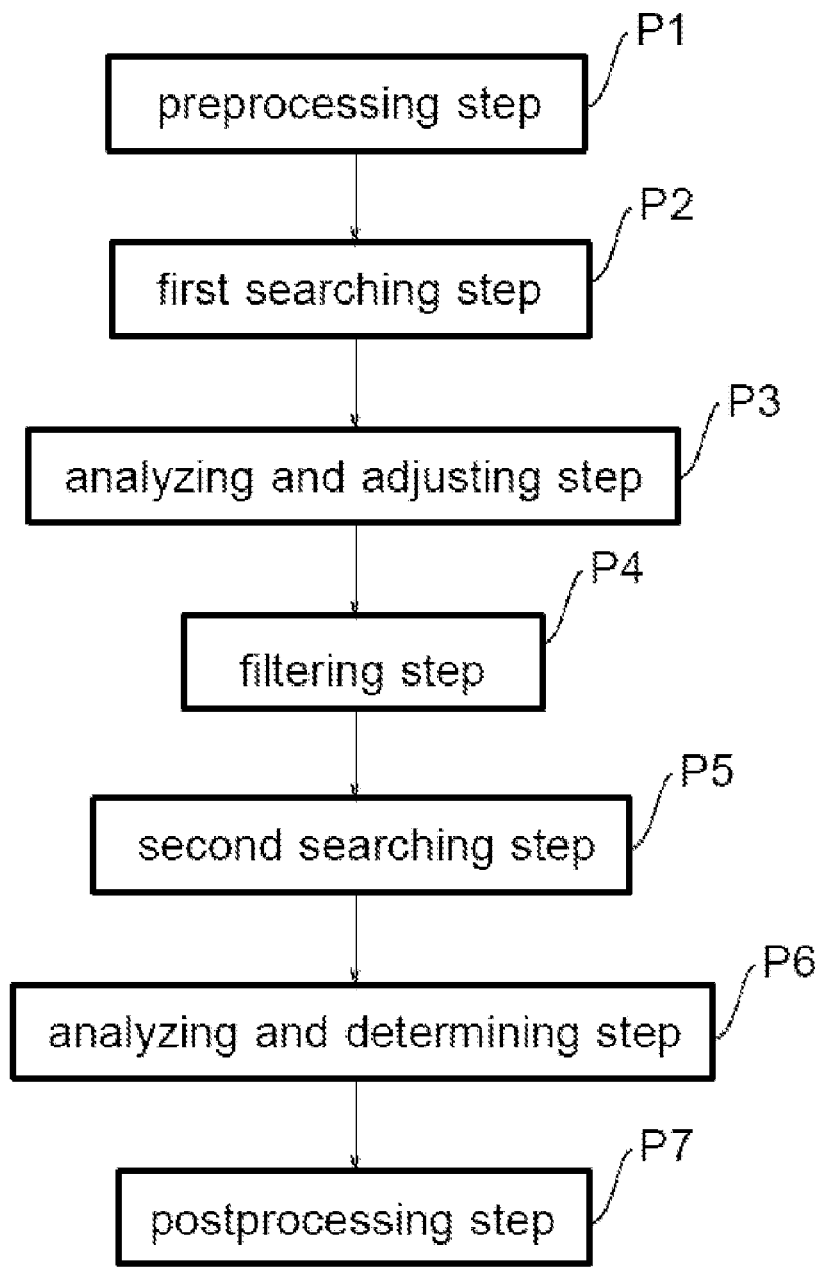
FIG. 3 is a schematic diagram illustrating the steps for the cerebral hemorrhage segmentation.

The cerebral hemorrhage segmentation to be performed on the apparatus will be described in greater details herein below. FIG. 3 shows steps of cerebral hemorrhage segmentation. As shown in FIG. 3, the cerebral hemorrhage segmentation is performed through seven steps P1 to P7.

The process step P1 is a preprocessing step. The process step P2 is a first searching step. The process step P3 is an analyzing and adjusting step. The process step P4 is a filtering step. The process step P5 is a secondary searching step. The process step P6 is an analyzing and determining step. Finally the process step P7 is a postprocessing step.

These steps are executed by the data processing unit 10. The data processing unit 10 is an example of the preprocessing means, an example of the primary searching means, an example of the analyzing and adjusting means, an example of the filtering means, an example of the secondary searching means, an example of the analyzing and determining means, and an example of the postprocessing means. These steps will be described in greater details herein below.

Figure 4:
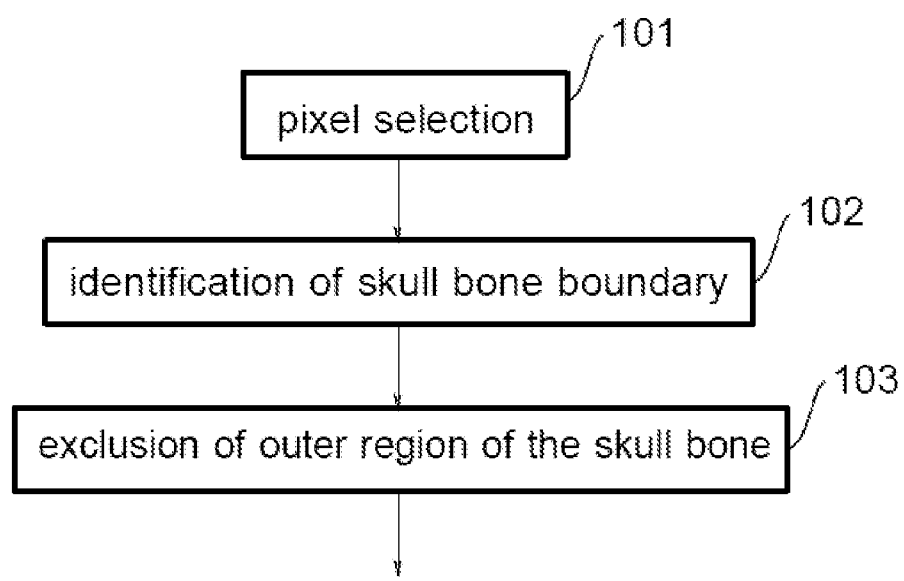
FIG. 4 is a schematic diagram illustrating the details of the preprocessing step.

FIG. 4 shows detailed substeps of the preprocessing step P1. As shown in FIG. 4, the preprocessing step P1, in step 101, selects pixels of an X-ray CT image of a head. The pixel selection is by excluding the pixels having a CT value larger than a first setting value and the pixels having a CT value less than a second setting value from the entire image. The first setting value may be 245, and the second setting value may be for example 30. Therefore the pixels having a CT value larger than 245 and the pixels having a CT value less than 30 will be excluded.

In step 102 the skull boundary is identified. The identification of the skull boundary is performed based on a third setting value. The identification of the skull boundary is by detecting for the entire image any CT value changing points from a value less than the third setting value to a larger value, or any CT value changing point from a value more than the third setting value to a lesser value. The third setting value may be for example 190. Based on the skull boundary thus identified, the external region of the skull bone is excluded in step 103, thus the internal region of the skull bone is segmented.

Figure 5:
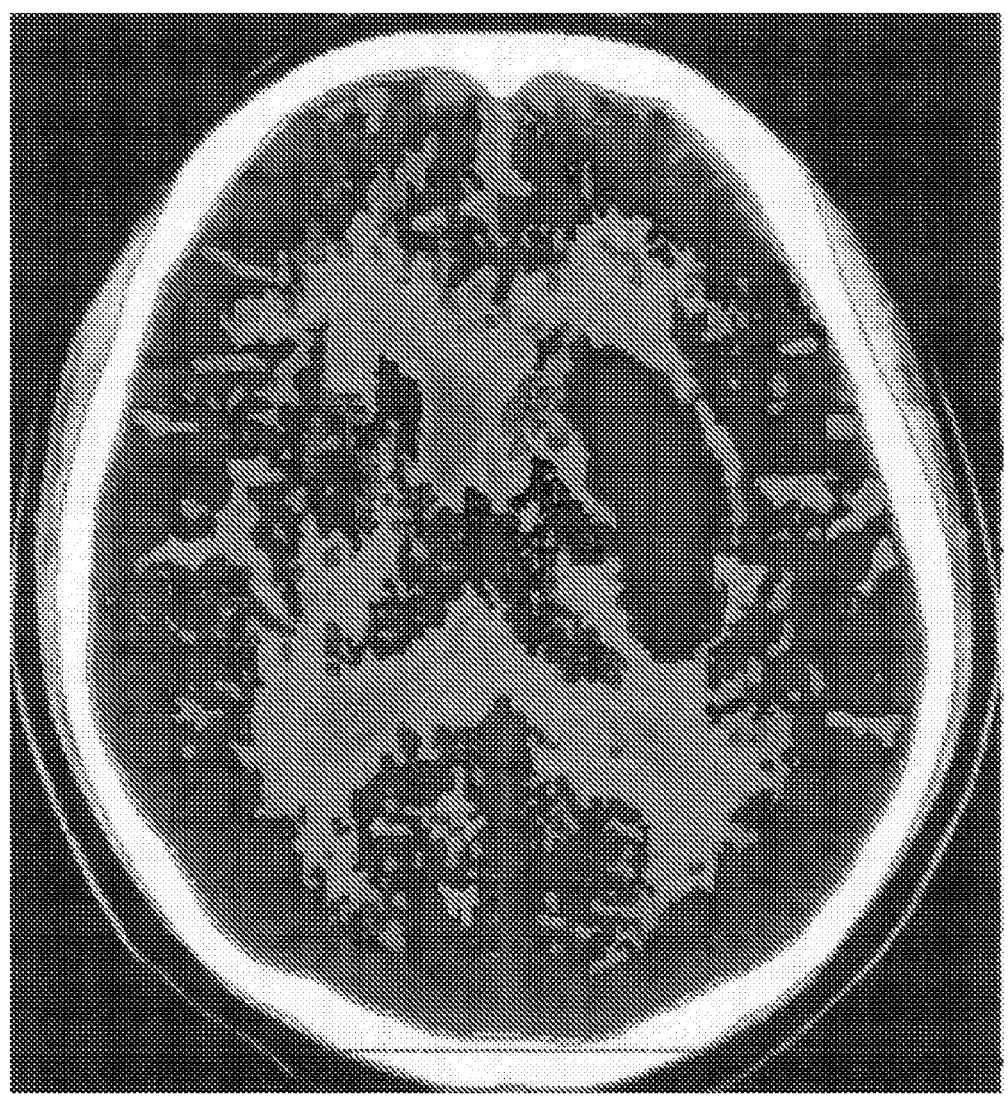
FIG. 5 is a schematic diagram illustrating an exemplary X-ray CT image after the preprocessing step as gray-scale photograph.

In steps 101 to 103, any pixels having a CT value larger than 245, and pixels having a CT value less than 30, and the region external to the skull bone are excluded. By the preprocessing as such, an image such as shown in FIG. 5 may be obtained. In FIG. 5, region blotted by black is indicative of a region not excluded. This black region is the target of next processing step.

Figure 6:
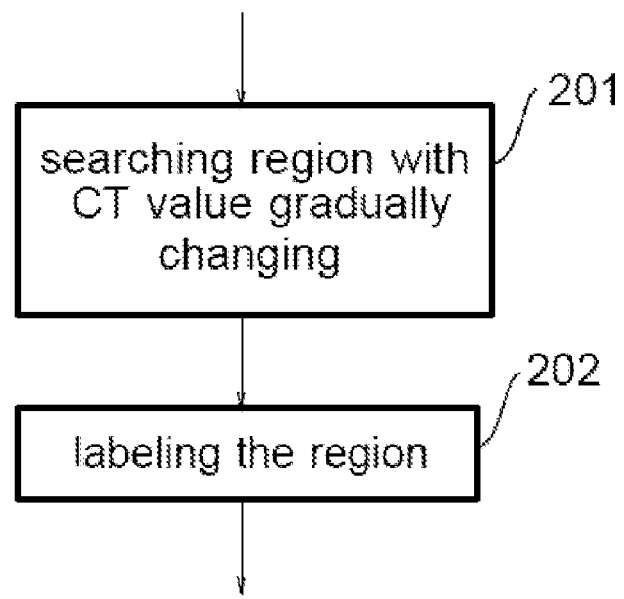
FIG. 6 is a schematic diagram illustrating the details of the primary searching step.

FIG. 6 shows detailed substeps of the primary searching step P2. As shown in FIG. 6, in primary searching step P2, on the preprocessed image, a region in which the CT value changes gradually is searched in step 201. The search for the region having a gradually changing CT value is by searching any region that a difference of the CT value between adjacent two pixels is 5 or less for example.

In step 202 the regions detected by the search are labeled, thus the region having a gradually changing CT value is segmented.

Figure 7:
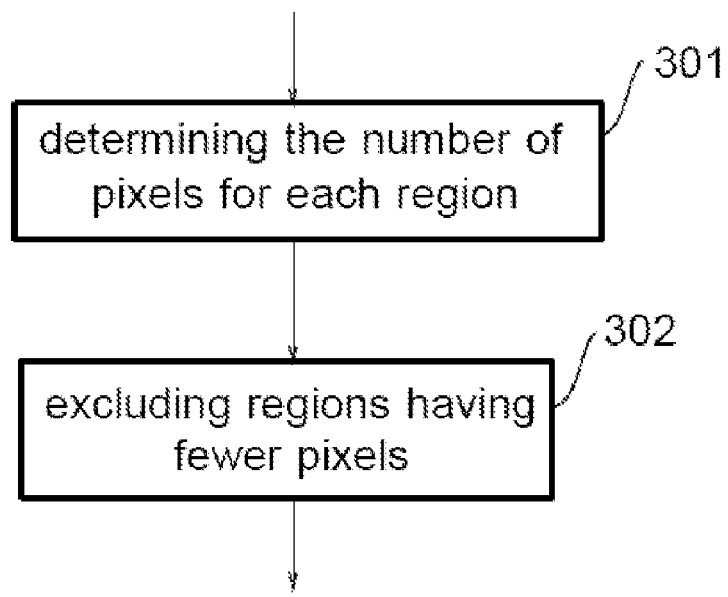
FIG. 7 is a schematic diagram illustrating the details of the analyzing and adjusting step.

FIG. 7 shows detailed substeps of the analyzing and adjusting step P3. As shown in FIG. 7, in the analyzing and adjusting step P3, the image having the primary search performed is counted region by region the number of pixels in step 301. In step 302 any region having the number of pixels less than a fourth setting value is excluded, thus the region having the number of pixels no less than a fourth setting value is segmented.

The fourth setting value may be for example 300, when defined field of view (defined FOV) is 25 cm. The setting value may be adjusted to an appropriate value other than 300 if the defined FOV is not 25 cm.

Figure 8:
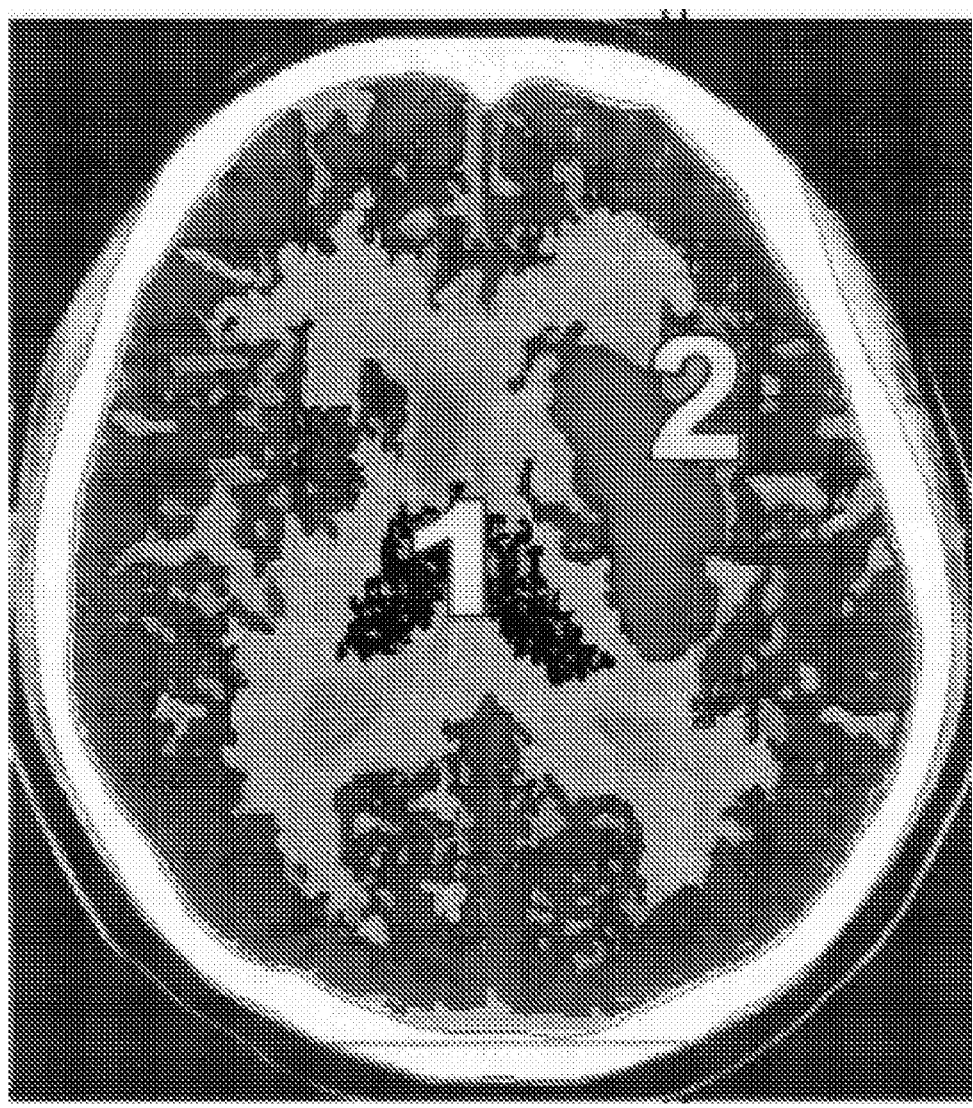
FIG. 8 is a schematic diagram illustrating an exemplary X-ray CT image after the primary searching and the analyzing and adjusting step as gray-scale photograph.

From the primary searching and the analyzing and adjusting as described above, an image such as shown in FIG. 8 can be obtained. In FIG. 8, the region blotted by black is indicative of the region having the number of pixels of 300 or over and a gradual CT value change. This region becomes the target of the next processing step.

Figure 9:
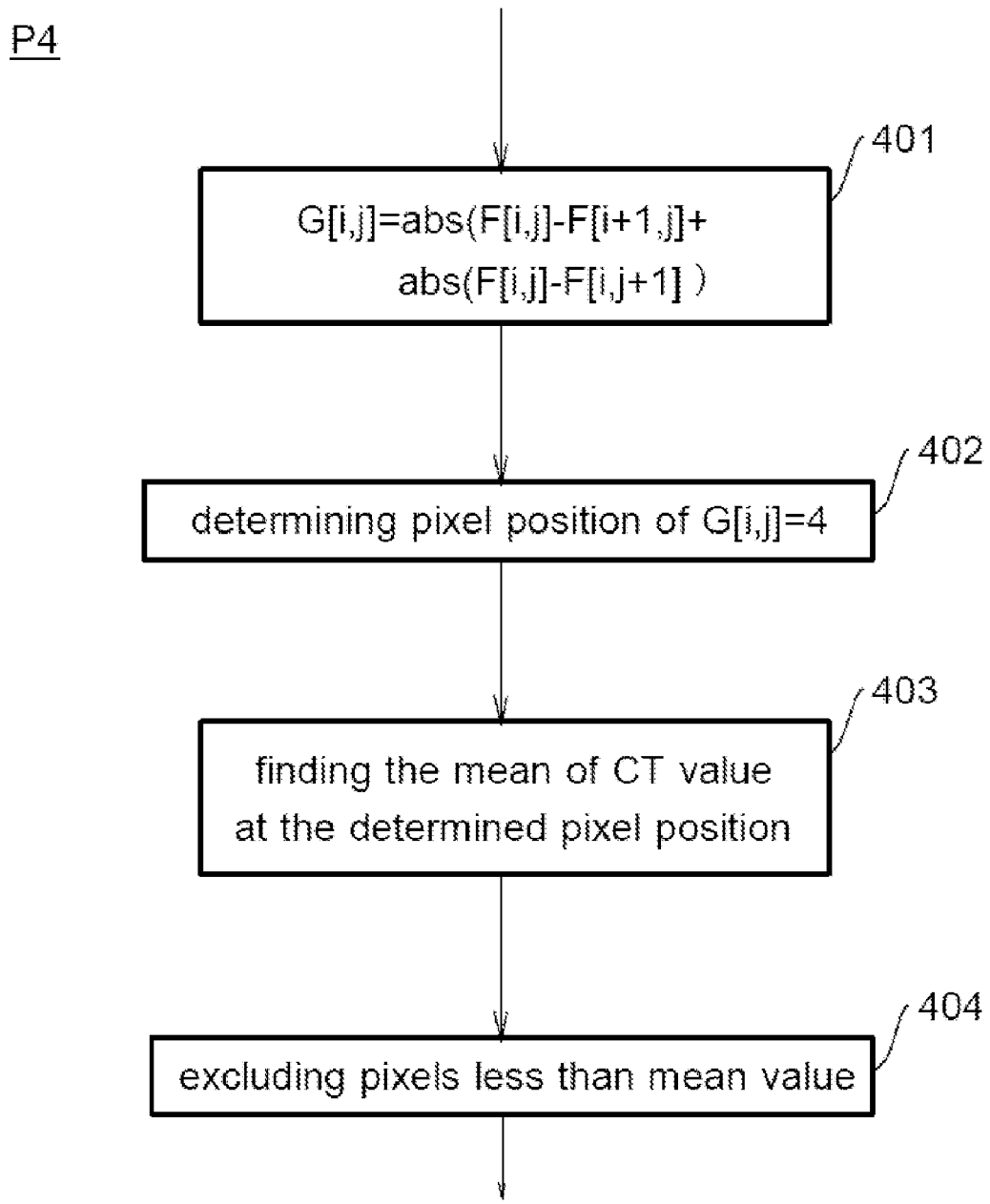
FIG. 9 is a schematic diagram illustrating the details of the filtering step.
Figure 10:
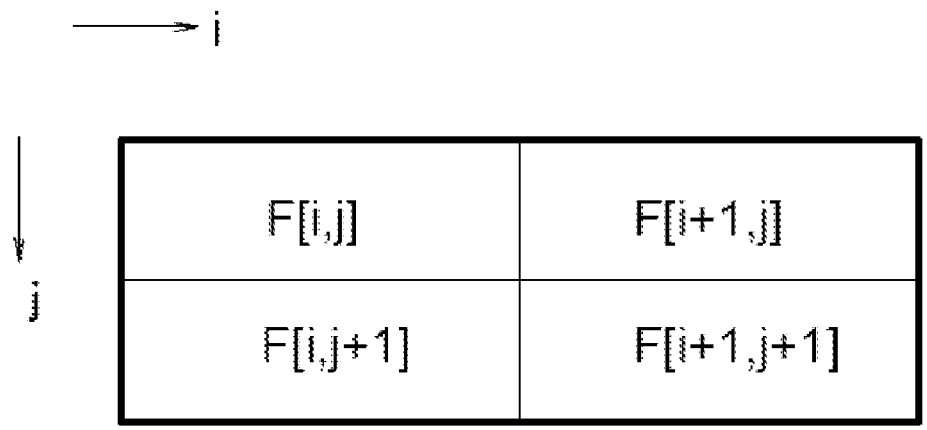
FIG. 10 is a schematic diagram illustrating the spatial positional relationships between pixel values.

FIG. 9 shows detailed substeps of the filtering step P4. As shown in FIG. 9, the filtering step P4 determines, on the image that has been analyzed and adjusted, pixel by pixel the sum of the absolute value of the difference of CT value between adjacent two pixels in the direction that two dimensional coordinate i, j increases, for each pixel and for each region, in step 401. In other words a calculation as shown below is performed using the following equation.

$$G[i,j]=abs(F[i,j]-F[i+1,j])+abs(F[i,j]-F[i,j+1]) \quad \text{Eq. (9)}$$

where F[i, j] is the CT value of the pixel at the two-dimensional coordinate i, j; F[i+1, j] is the CT value of an adjacent pixel in the direction that the coordinate i is incrementing; F[i, j+1] is the CT value of an adjacent pixel in the direction that the coordinate j is incrementing. The relationship among CT values F[i, j], F[i+1, j], F[i, j+1], and F[i+1, j+1] is as shown in FIG. 10.

In step 402, a pixel position is identified where G[i, j] becomes more than the fifth setting value. The fifth setting value may be for example 4. In step 403, a mean value of the CT values at all of the pixel positions identified is determined, and in step 404 any pixels having a CT value equal to or less than the mean value is excluded, thus the region with remained pixels is segmented.

The mean of the CT value is determined from the original image for each region. The exclusion of pixels having a CT value equal to or less than the mean value is performed on the original image region by region. This allows the removal of background for each region.

Figure 11:
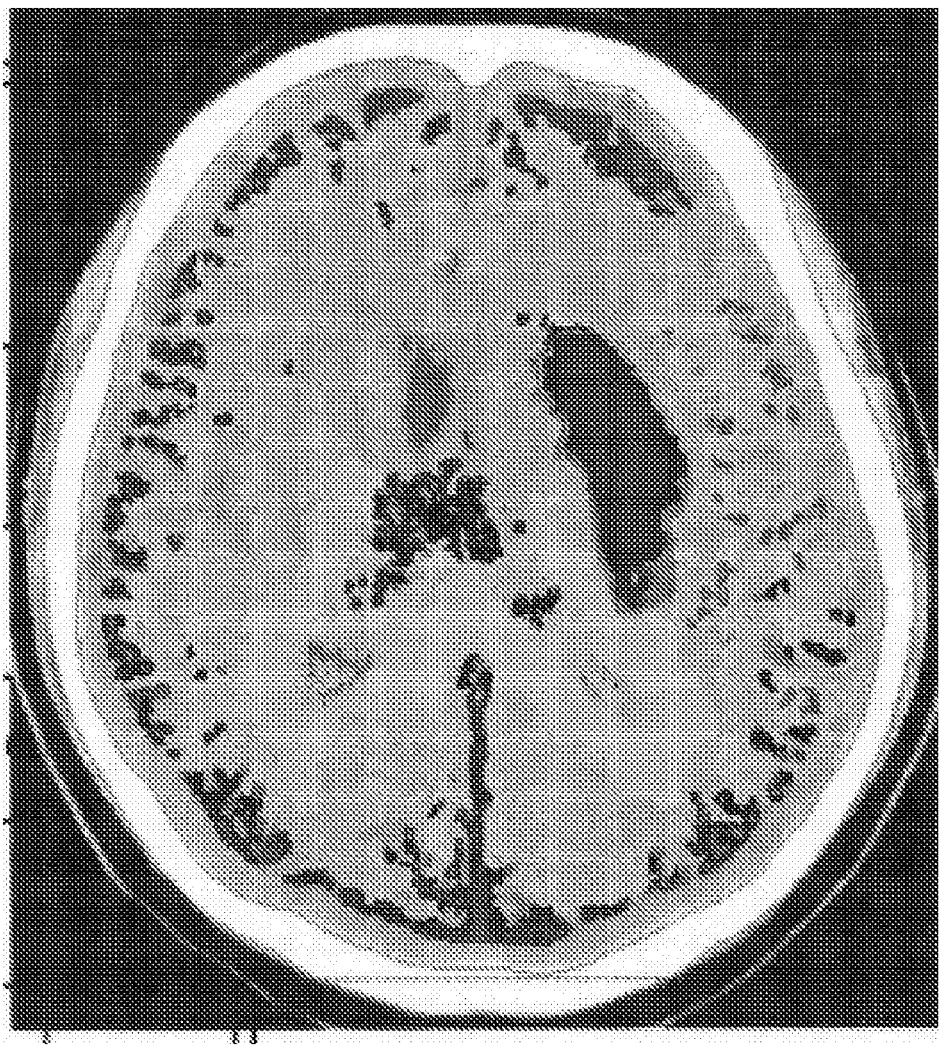
FIG. 11 is a schematic diagram illustrating an exemplary X-ray CT image after the filtering step as gray-scale photograph.

By the filtering as described above, an image such as shown in FIG. 11 can be obtained. In FIG. 11, the region blotted by black is indicative of the region not excluded. This black region is the target of the next process step.

Figure 12:
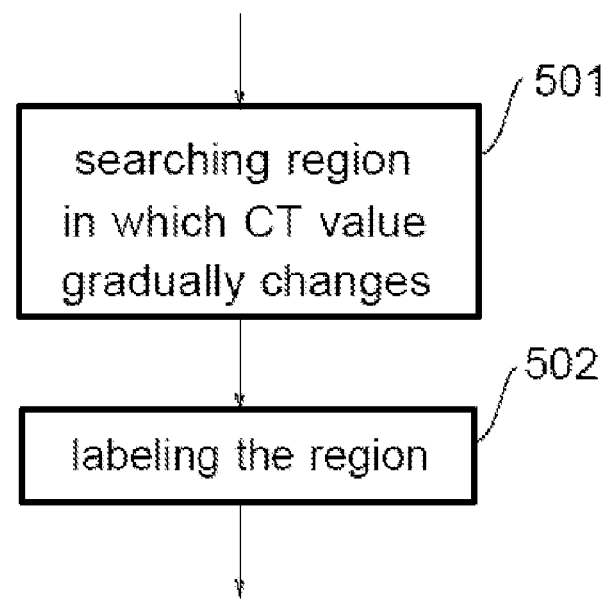
FIG. 12 is a schematic diagram illustrating the details of the secondary searching step.
Figure 13:
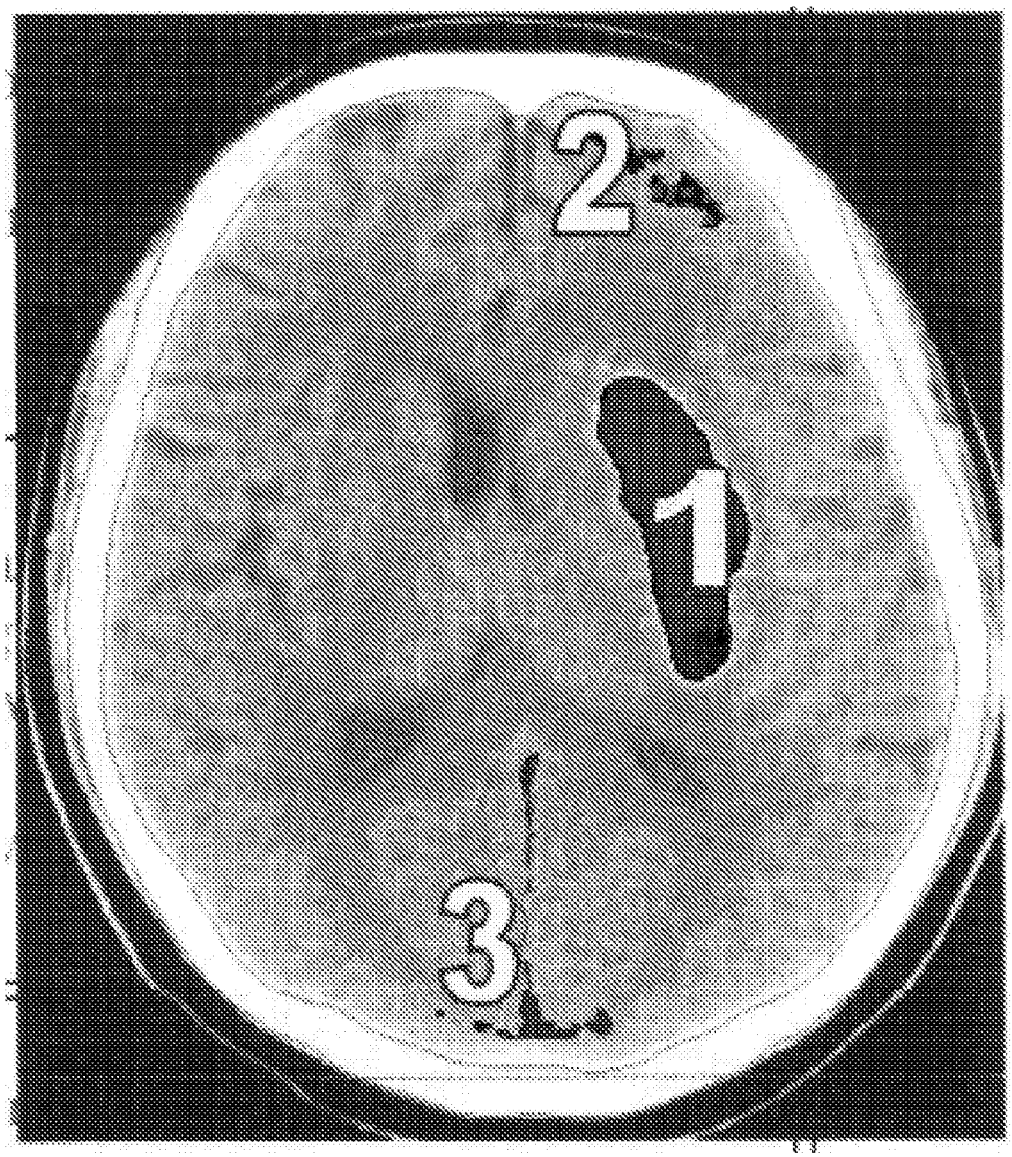
FIG. 13 is a schematic diagram illustrating an exemplary X-ray CT image after the secondary searching as gray-scale photograph.

FIG. 12 shows detailed substeps of the secondary searching step P5. As shown in FIG. 12, the secondary searching step P5 searches regions having CT value gradually changing, in step 501, for the filtered image. The search for regions having CT value gradually changing is by searching the region that the difference of CT value between adjacent two pixels is equal to or less than 5. In step 502, the regions found by searching are newly labeled, thus the region having CT value gradually changing is segmented. By the secondary searching as described above, an image such as shown in FIG. 13 can be obtained that includes regions 1, 2, and 3.

Figure 14:
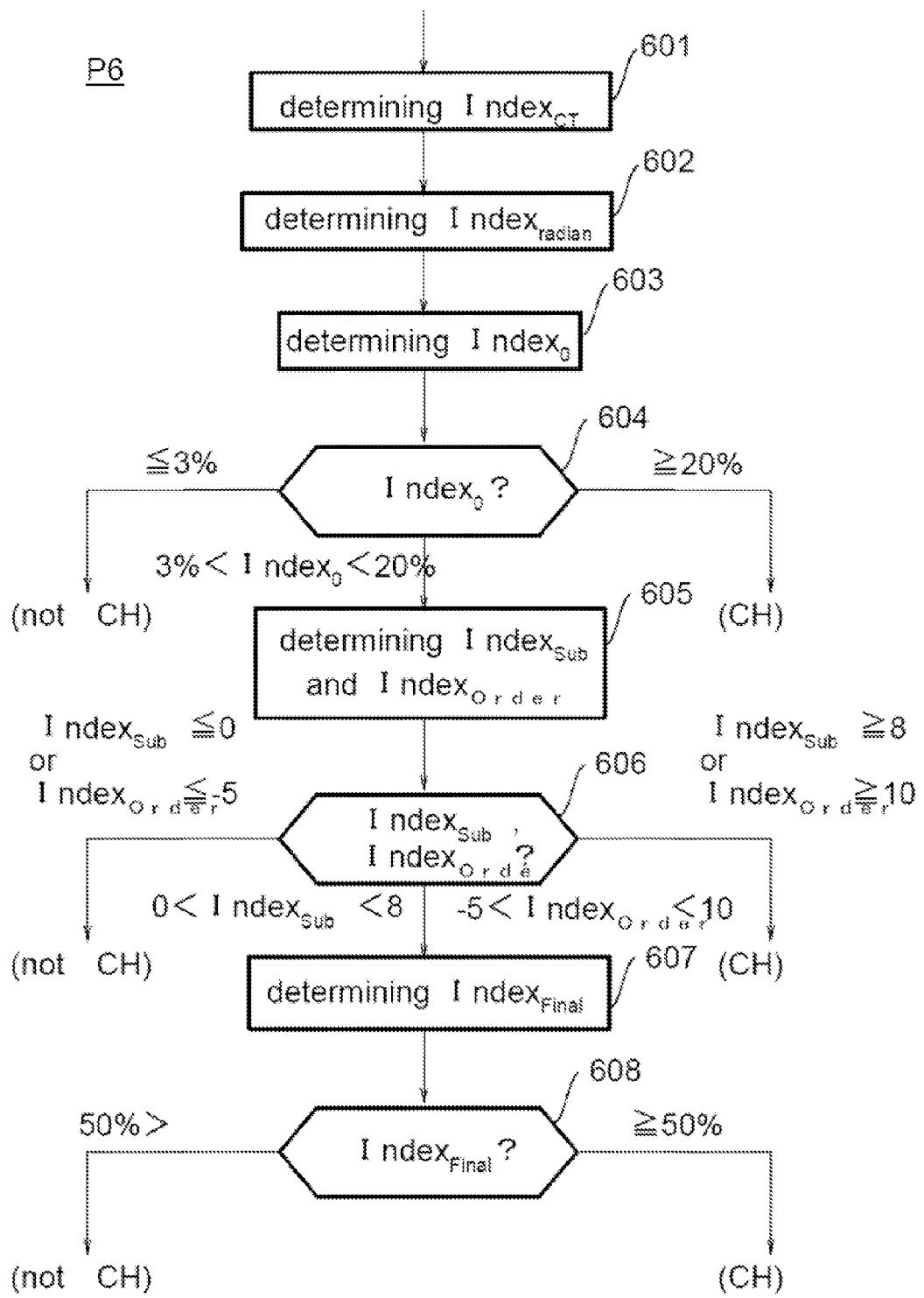
FIG. 14 is a schematic diagram illustrating the details of the analyzing and determining step.

FIG. 14 shows detailed substeps of the analyzing and determining step P6. As shown in FIG. 14, in the analyzing and determining step P6, a first index $Index_{CT}$ is determined for the labeled image on which the second search has been performed in step 601.

The index Indexcт sets $$Index_{CT}=(CT_{Region}-CT_{min})/(CT_{blood}-CT_{Min}) \quad \text{Eq. (1)}$$

if $CT_{min}<=CT_{Region}<=CT_{Blood}$, or $$Index_{CT}=(CT_{max}-CT_{region})/(CT_{max}-CT_{blood}) \quad \text{Eq. (2)}$$

if $CT_{Blood}<CT_{Region}<=CT_{max}$, or else sets $Index_{CT}=0$ where $CT_{Region}$ is the CT value of the region pixels, $CT_{max}$ is the sixth setting value, $CT_{min}$ is the seventh setting value, and $CT_{Blood}$ is the eighth setting value.

Here, the sixth setting value $CT_{max}$ may be for example 100, the seventh setting value $CT_{min}$ may be for example 40, and the eighth setting value $CT_{Blood}$ may be for example 70.

In step 602, a second index $Index_{Radian}$ is determined. In the second index $Index_{Radian}$, when the surface area and the perimeter length of the region is identified as Area and Perimeter, and the characteristics value of the region is identified as $$Radian=Area/Perimeter2 \quad \text{Eq. (3)},$$

$Index_{Radian}=1$ if Radian is larger than the ninth setting value $Radian_{max}$, $Index_{Radian}=0$ if Radian is less than the tenth setting value $Radian_{min}$ and $$Index_{radian}=(Radian_{region}-Radian_{Min})/(Radian_{Max}-Radian_{Min}) \quad \text{Eq (4)}$$

if Radian is less than or equal to the ninth setting value $Radian_{max}$ and more than or equal to the tenth setting value $Radian_{min}$.

Here the ninth setting value $Radian_{max}$ may be for example 0.015, the tenth setting value $Radian_{min}$ may be for example 0.003.

In step 603, a third index $index_0$ is set to $$Index_0=Index_{CT}*Index_{radian}. \quad \text{Eq. (5)}$$

In step 604, it is determined whether the region of interest has a cerebral hemorrhage or not in accordance with the value of third index $index_0$. More specifically, if $index_0>=20\%$ then the region has a cerebral hemorrhage (CH), if $index_0<=3\%$ then the region has not a cerebral hemorrhage (not CH), else if $3\%<index_0<20\%$ then the process proceeds to the next step 605.

In step 605, the fourth index $Index_{sub}$ and the fifth index $Index_{Order}$ are determined. More specifically, the fourth index $Index_{sub}$ is set to $$Index_{sub}=CT_{Region}-CT_{AroundRegion} \quad \text{Eq. (6)}$$

and the fifth index $Index_{Order}$ is set to $$Index_{Order}=CT_{Region}-CT_{Average-All-Region} \quad \text{Eq. (7)}$$

when the CT value of the pixels of the surrounding region around the region $3\%<index_0<20\%$ is $CT_{AroundRegion}$ and the mean CT value of the entire region which is $3\%<index_0<20\%$ is $CT_{Average-All-Region}$.

In step 606, it is determined whether the region of interest has a cerebral hemorrhage or not in accordance with the value of the fourth index $Index_{sub}$ and with the value of the fifth index $Index_{Order}$. More specifically, a region is determined to have a cerebral hemorrhage (CH) if $Index_{sub}>=8$ or $Index_{Order}>=10$, or a region is determined not to have a cerebral hemorrhage (not CH) if $Index_{sub}<=0$ or $Index_{Order}<=-5$, else the process goes to next step 607 if $0<Index_{sub}<8$ and $-5<Index_{Order}<10$.

In step 607, the sixth index $Index_{Final}$ is set to $$Index_{Final}=Index_0*(Index_{Order}-(-5))/(10-(-5)) \quad \text{Eq. (8)}$$

In step 608, a region is determined whether or not to have a cerebral hemorrhage in correspondence with the value of the sixth index $Index_{Final}$. More specifically, a region is determined to have a cerebral hemorrhage (CH) if $Index_{Final}>=50\%$, otherwise a region is determined not to have a cerebral hemorrhage (not CH) if $Index_{Final}<50\%$.

Figure 15:
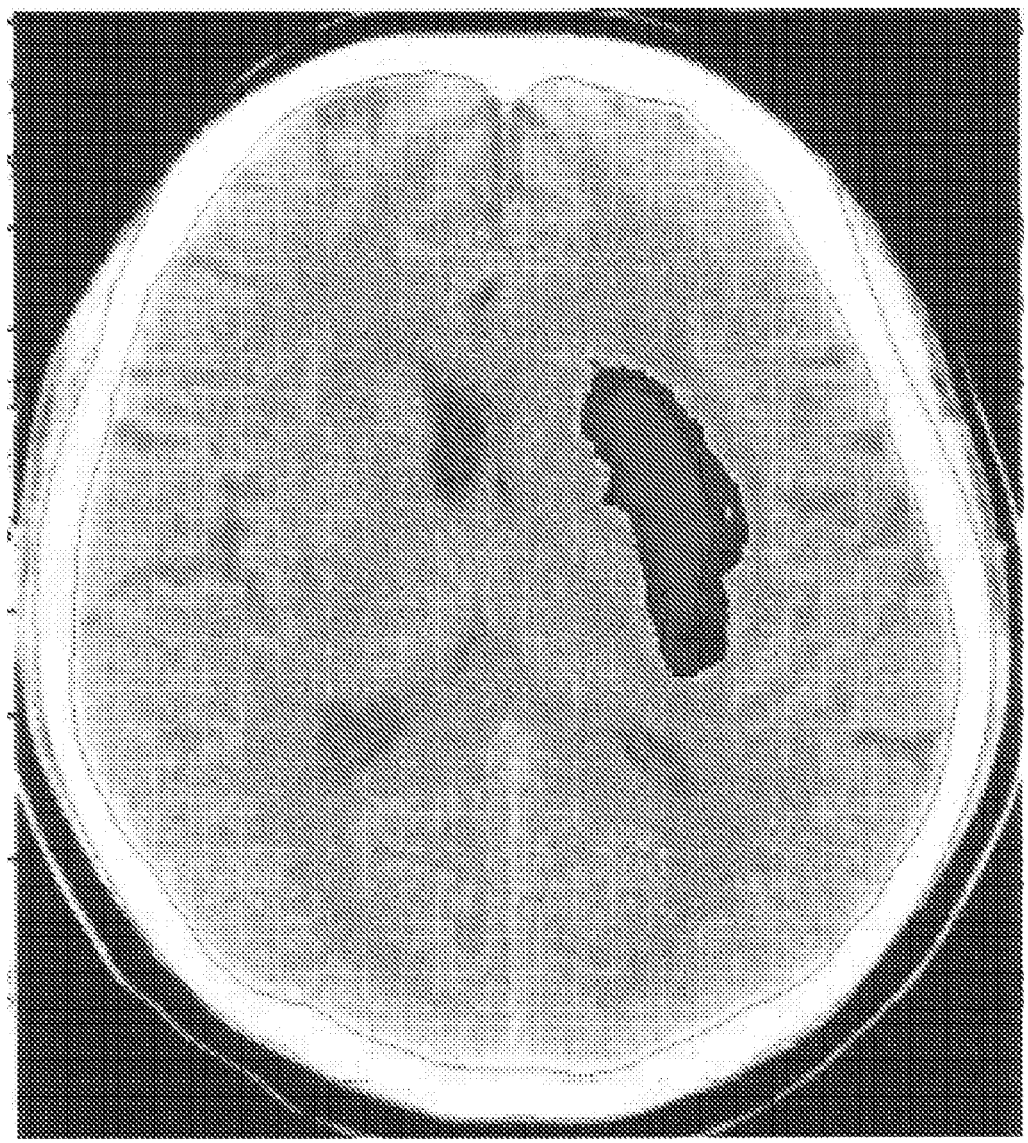
FIG. 15 is a schematic diagram illustrating an exemplary X-ray CT image after analyzing and determining step as gray-scale photograph.

An accurate segmentation of a cerebral hemorrhage region is then performed in accordance with the three-step-analyze and determination as have been described above, and an image such as shown in FIG. 15 may be obtained. In FIG. 15, the region blotted by black is indicative of a cerebral hemorrhage. The region blotted by black indicates the actual position and extent of cerebral hemorrhage with a high precision.

When the cerebral hemorrhage is in proximity of the skull bone, the partial volume effect may cause the CT value of the cerebral hemorrhage region to be changed, resulting in an inaccurate segmentation of the cerebral hemorrhage.

Figure 16:
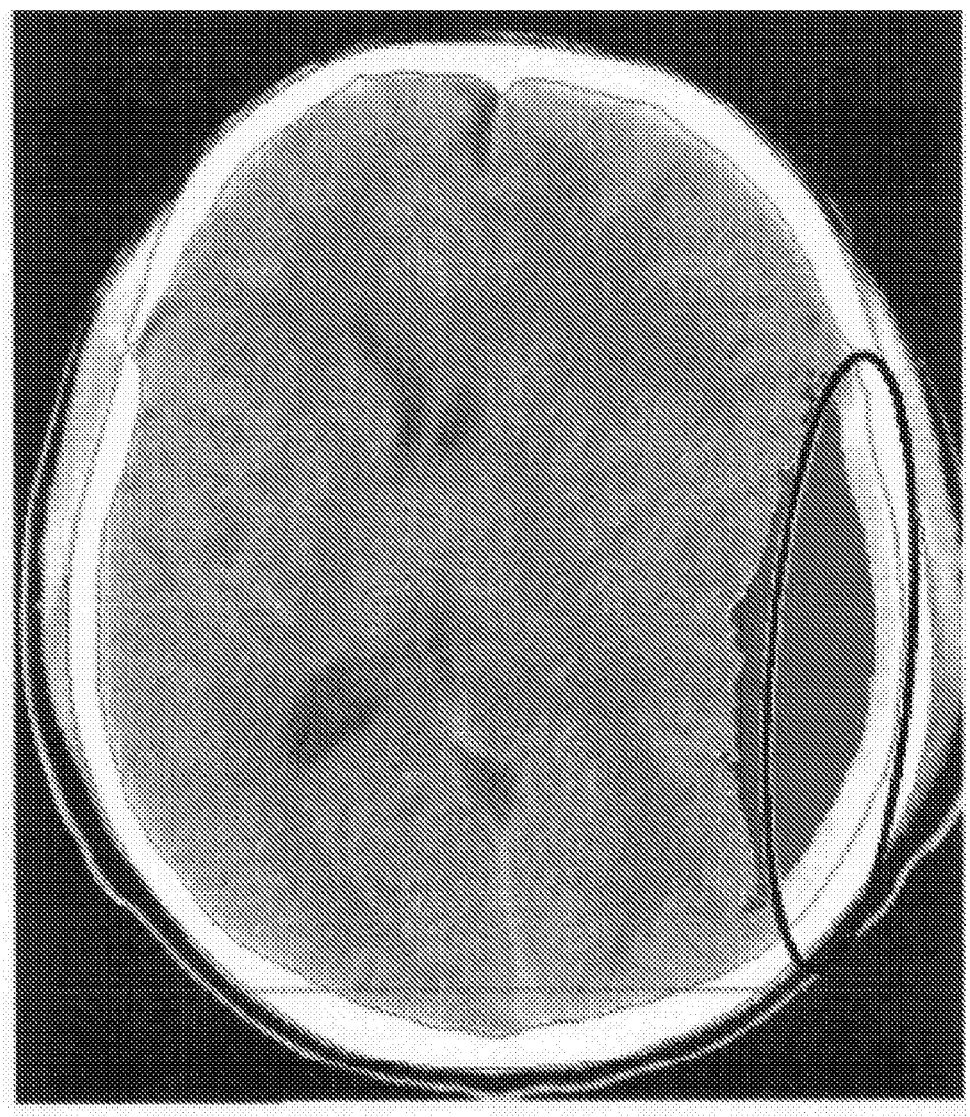
FIG. 16 is a schematic diagram illustrating an exemplary X-ray CT image after analyzing and determining step as gray-scale photograph.

FIG. 16 shows an example. In FIG. 16 the region blotted by black is the region segmented. The contour of this region at the right hand side does not reach the skull bone boundary. This is because the CT value which has been changed due to the partial volume effect was excluded. The segmentation result as described above may be compensated for the influence of the partial volume effect in the postprocessing step P7.

Figure 17:
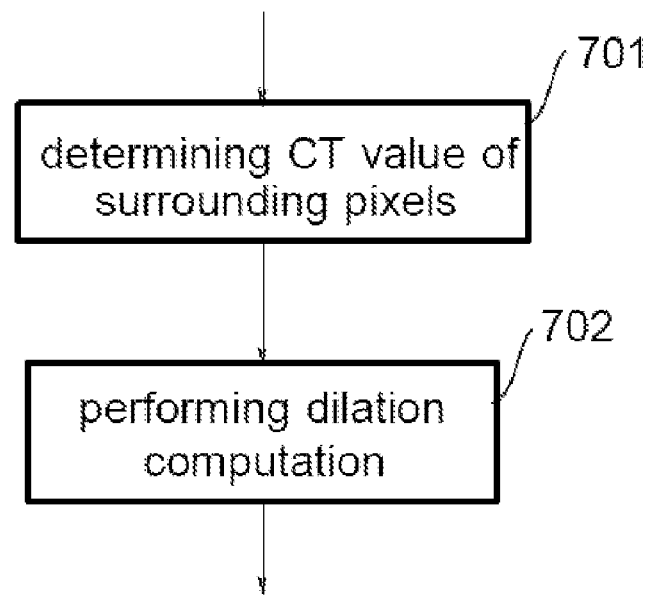
FIG. 17 is a schematic diagram illustrating the details of the postprocessing step.
Figure 18:
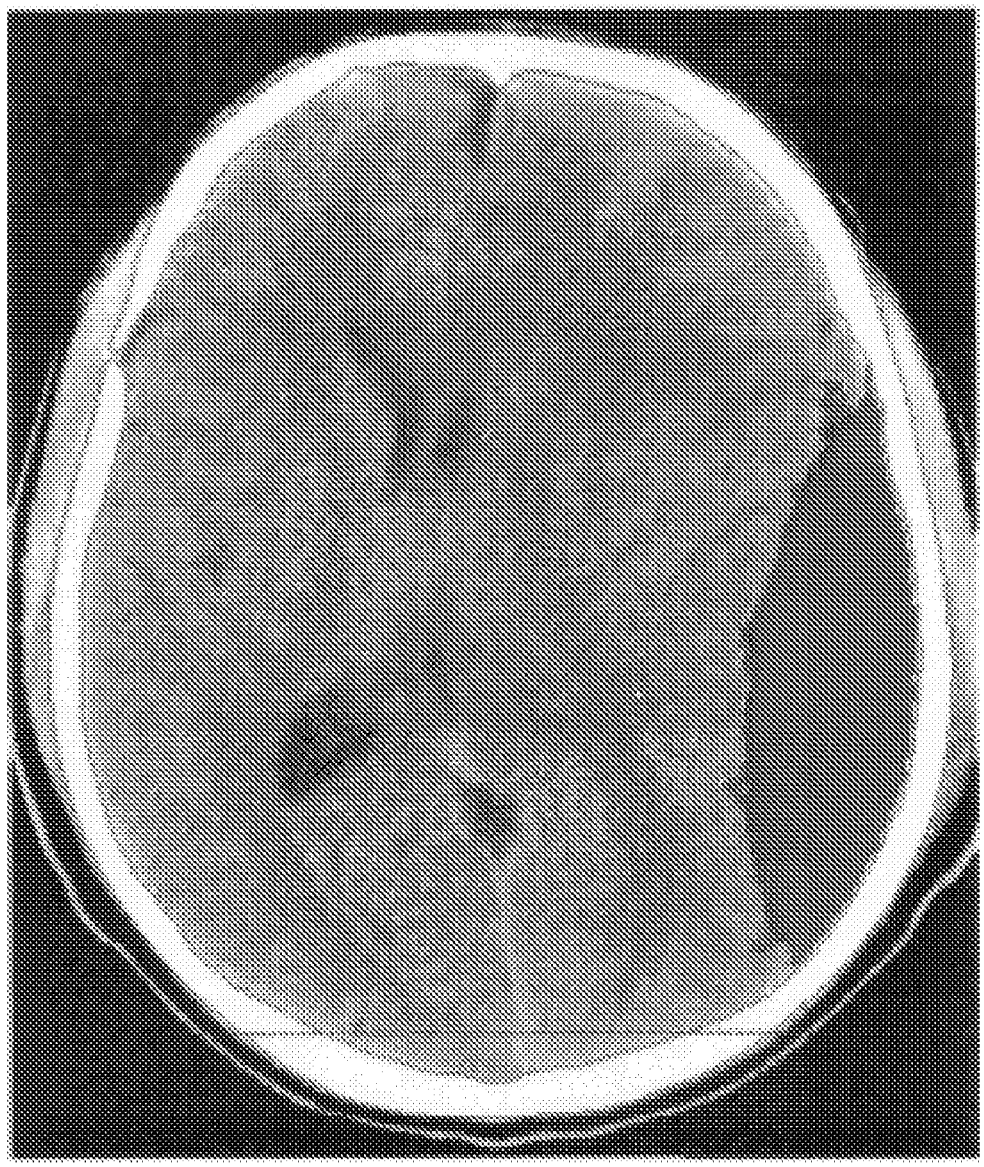
FIG. 18 is a schematic diagram illustrating an exemplary X-ray CT image after postprocessing step as gray-scale photograph.

FIG. 17 shows detailed substeps of the postprocessing step P7. As shown in FIG. 17, in the postprocessing step P7, the region that has been determined to have a cerebral hemorrhage by the analyzing and determining, namely the CH region, is determined whether or not to have the CT value of the surrounding pixels larger than the mean CT value of the CH region in step 701. If the CT value of the surrounding pixels is larger, then a dilation calculation is performed until the perimeter of the CH region reaches the skull bone boundary. With this postprocessing, as shown in FIG. 18, an image with the influence of the partial volume effect being compensated for on the CH region may be obtained.

What is claimed is;

1. A method of segmenting a cerebral hemorrhage site in a medical image of a head, said method comprising:
    segmenting, using a data processing unit, an internal region of a skull bone in the medical image;
    segmenting, using the data processing unit, a possible cerebral hemorrhage region out of the internal region of the skull bone by
        segmenting a region with CT values gradually changing out of the internal region of the skull bone;
        segmenting a region with a number of pixels larger than a predetermined number, out of the region segmented in said step of segmenting a region with CT values gradually changing;
        segmenting a region with a comparatively large CT value out of the region segmented in said step of segmenting a region with a number of pixels larger than a predetermined number; and
        segmenting a region with CT values gradually changing out of the region segmented in said step of segmenting a region with a comparatively large CT value; and
    determining a cerebral hemorrhage site within the possible cerebral hemorrhage region.

2. A method of segmenting a cerebral hemorrhage site according to claim 1, wherein determining a cerebral hemorrhage site comprises:
    for the region segmented in said step of segmenting a possible cerebral hemorrhage region, a first step of determining whether the possible cerebral hemorrhage region includes a cerebral hemorrhage site based on a CT value and a size of the possible cerebral hemorrhage region; and for a potential region of the cerebral hemorrhage site out of a region other than the region which has been determined as the cerebral hemorrhage site in said first step, a second step of determining whether the potential region is the cerebral hemorrhage site based on a CT value difference between the potential region and a vicinity thereof or a CT value of the region.

3. A method of segmenting a cerebral hemorrhage site according to claim 1, further comprising correcting an influence of a partial volume effect for the cerebral hemorrhage site.

4. A method for cerebral hemorrhage segmentation by an X-ray CT image of a head, said method comprising:

preprocessing the X-ray CT image of the head, including:
excluding pixels having a CT value larger than a first setting value and pixels having a CT value less than a second setting value;
identifying a skull bone boundary based on a third setting value; and
excluding an external region of a skull bone based on the identified boundary;

primary searching the preprocessed image including:
searching a region with a CT value gradually changing; and
labeling each region found by the search;

analyzing and adjusting the primary searched image including:
determining a number of pixels for each region; and
excluding a region that has a respective number of pixels less than a fourth setting value;

filtering the analyzed and adjusted image including:
for each region, determining pixel by pixel a sum of an absolute value of a difference of the CT value between two pixels adjacent in a direction that a twodimensional coordinate i,j is increasing;
identifying a pixel position at which the sum is more than a fifth setting value;
determining a mean of CT values in all of the identified pixel positions; and
excluding pixels having a CT value equal to or less than the mean value;

secondary searching the filtered image including:
searching the region with the CT value gradually changing; and
newly labeling each region identified by the search;

analyzing and determining the labeled image including:
setting a first $Index_{CT}$ to one of $Index_{CT}=(CT_{Region}-CT_{min})/(CT_{blood}-CT_{Min})$ if $CT_{min}<=CT_{Region}<=CT_{Blood}$, $Index_{CT}=(CT_{max}-CT_{region})/(CT_{max}-CT_{blood})$ if $CT_{Blood}<CT_{Region}<=CT_{max}$, and $Index_{CT}=0$, where $CT_{Region}$ is the CT value of the pixel of said region, $CT_{max}$ is a sixth setting value, $CT_{min}$ is a seventh setting value, $CT_{Blood}$ is an eighth setting value, where a surface area and a perimeter length of each region is identified as Area and Perimeter, and a characteristics value of each region is identified as Radian =Area/Perimeter$^2$ ;
setting a second index $Index_{Radian}$ to one of $Index_{Radian}=1$ if Radian is more than a ninth setting value $Radian_{max}$, $Index_{Radian}=0$ if Radian is more than a ninth setting value $Radian_{min}$, and $Index_{radian}=(Radian_{region}-Radian_{Min})/(Radian_{max}-Radian_{Min})$ if Radian is equal to or less than the ninth setting value $Radian_{max}$ and equal to or more than the tenth setting value $Radian_{min}$;
setting a third index $Index_0$ to $Index_0=Index_{CT}*Index_{radian}$;
one of determining that each region has a cerebral hemorrhage if $index_0>=20\%$, determining that the region has not a cerebral hemorrhage if $index_0<=3\%$ , and setting a fourth index $Index_{Sub}$ to $Index_{Sub}=CT_{Region}-CT_{AroundRegion}$ when $3\%<index_0<20\%$, where $CT_{AroundRegion}$ is the CT value of the pixel of the surrounding region around the region, and $CT_{Average-All-Region}$ is the mean CT value of all such regions;
setting a fifth index $Index_{Order}$ to $Index_{Order}-=CT_{Region}-CT_{Average=All=Region}$;
one of determining that the region has a cerebral hemorrhage if $Index_{sub}>=8$ or $Index_{Order}>=10$, determining that the region has not a cerebral hemorrhage if $Index_{sub}<=0$ or $Index_{Order}<=-5$, and setting a sixth index $Index_{Final}$ to $Index_{Final}=Index_0*(Index_{Order}-(-5))/(10-(-5))$ if $0<Index_{sub}<8$ and $-5<Index_{Order}<10$, then one of determining that the region has a cerebral hemorrhage if $Index_{Final}>=50\%$ and determining that the region has not a cerebral hemorrhage if $Index_{Final}<50\%$; and
compensating for an influence of a partial volume effect on the region determined to have a cerebral hemorrhage.

5. A method for cerebral hemorrhage segmentation according to claim 4, wherein:
identifying a skull bone boundary comprises detecting a CT value changing point from a value smaller than the third setting value to a larger value or a CT value changing point from a value larger than the third setting value to a smaller value.

6. A method for cerebral hemorrhage segmentation according to claim 4, wherein:
each of said primary searching and said secondary searching comprises searching a region where the difference of CT value between adjacent two pixels is equal to or less than 5.

7. A method for cerebral hemorrhage segmentation according to claim 4, wherein:
compensating comprises performing a dilation calculation with respect to the region.

8. A method for cerebral hemorrhage segmentation according to claim 4, wherein:
the first setting value is 245, the second setting value is 30, the third setting value is 190, the fourth setting value is 300, the fifth setting value is 4, the sixth setting value is 100, the seventh setting value is 40, the eighth setting value is 70, the ninth setting value is 0.015, and the tenth setting value is 0.003.

9. An apparatus for segmenting a cerebral hemorrhage site in a medical image of a head, said apparatus comprising:
means for segmenting an internal region of a skull bone in an X-ray CT image of a head;
means for segmenting a possible cerebral hemorrhage region out of the internal region of the skull bone comprising:
means for segmenting a region with CT values gradually changing out of the internal region of the skull bone;
means for segmenting a region with a number of pixels larger than a predetermined number, out of the region segmented by said means for segmenting a region with CT values gradually changing;

means for segmenting a region with comparatively large CT value out of the region segmented by said means for segmenting a region with the number of pixels larger than a predetermined number; and means for segmenting a region with CT values gradually changing out of the region segmented by said means for segmenting a region with comparatively large CT value; and means for determining a cerebral hemorrhage within the possible cerebral hemorrhage region.

10. An apparatus for segmenting a cerebral hemorrhage site according to claim 9, wherein said means for determining a cerebral hemorrhage site comprises:

for the region segmented by said means for segmenting the possible cerebral hemorrhage region, first means for determining whether the segmented region is a cerebral hemorrhage site based on a CT value and a size of the segmented region; and for a potential region of the cerebral hemorrhage site out of a region other than the region which has been determined as the cerebral hemorrhage site by said first means, second means for determining whether the potential region is the cerebral hemorrhage site based on a CT value difference between the potential region and a vicinity thereof or a CT value of the region.

11. An apparatus for segmenting a cerebral hemorrhage site according to claim 9, further comprising means for correcting an influence of a partial volume effect for the cerebral hemorrhage site.

12. An apparatus for cerebral hemorrhage segmentation on an X-ray CT image of a head, said apparatus comprising:

preprocessing means configured to:
exclude pixels having a CT value larger than a first setting value and pixels having a CT value less than a second setting value;
identify a boundary of the skull bone based on a third setting value; and
exclude an outer region of the skull bone based on the boundary identified;

primary searching means configured to:
search a region where the CT value gradually changes; and
label each region found by the search;

analyzing and adjusting means configured to:
determine a number of pixels for each region; and
exclude a region having a respective number of pixels less than a fourth setting value;

filtering means configured for each region to:
determine a sum of an absolute value of a difference of the CT value between adjacent pixels for each pixel in a direction wherein a two-dimensional coordinate i,j is increasing;
identify a pixel position at which the sum is more than a fifth setting value;
determine a mean value of CT values at all of the identified pixel positions; and
exclude pixels having a CT value less than the mean value;

secondary searching means configured to:
search a region where the CT value gradually changes; and
newly label each region found by the search;

analyzing and determining means configured to:
set a first index $Index_{CT}$ to one of $Index_{CT}=(CT_{Region}-CT_{min})/(CT_{blood}-CT_{Min})$ if $CT_{min}<=CT_{Region}<=CT_{Blood}$, $Index_{CT}=(CT_{max}-CT_{region})/(CT_{max}-CT_{blood})$ if $CT_{Blood<CTRegion}<=CT_{max}$, and $Index_{CT}=0$, where $CT_{Region}$ is the CT value of the pixel in the region, $CT_{max}$ is a sixth setting value, $CT_{min}$ is a seventh setting value, and $CT_{Blood}$ is an eighth setting value, where a surface area and a perimeter length of the region are indicated as Area and Perimeter, and a characteristics value of the region is indicated by Radian=Area/Perimeter$^2$;
set a second index $Index_{Radian}$ to one of $Index_{Radian}=1$ if Radian is more than a ninth setting value $Radian_{max}$, $Index_{Radian}=0$ if Radian is less than a tenth setting value $Radian_{min}$, and to $Index_{radian}=(Radian_{region}-Radian_{Min})/(Radian_{max}-Radian_{min})$ if Radian is less than or equal to the ninth setting value $Radian_{max}$ and more than or equal to the tenth setting value $Radian_{min}$;
set a third $Index_0$ to $Index_0=Index_{CT}*Index_{radian}$;
one of determine that the region has the cerebral hemorrhage if $index_{0>=}20\%$, determine that the region has not the cerebral hemorrhage if $index_0<=3\%$, and if $3\%<index_0<20\%$, and when $_{CTAroundRegion}$ is the CT value of the pixel of the surrounding region of the region, and $CT_{Average-All-Region}$ is the mean CT value of all regions, then set a fourth $Index_{sub}$ to $Index_{Sub}=CT_{Region}-CT_{AroundRegion}$;
set a fifth index $Index_{Order}$ to $Index_{Order}=CT_{Region}-CT_{Average-All-Region}$;
one of determine that the region has a cerebral hemorrhage if $Index_{sub}>=8$ or $Index_{Order}>=10$, determine that the region has not a cerebral hemorrhage if $Index_{sub}<=0$ or $Index_{Order}<=-5$, and, if $0<Index_{sub}<8$ and $-5<Index_{Order}<10$, then set a sixth index $Index_{Final}$ to $Index_{Final}=Index_0*(Index_{Order}-(-5))/(10-(-5))$; and
one of determine that the region has a cerebral hemorrhage if $Index_{Final}>=50\%$, and determine that the region has not a cerebral hemorrhage if $Index_{Final}<50\%$; and postprocessing means configured to compensate for an influence of partial volume effect on the region determined as having a cerebral hemorrhage.

13. An apparatus for cerebral hemorrhage segmentation according to claim 12, wherein:
said preprocessing means is configured to identify the skull boundary by detecting one of a CT value changing point from a value smaller than the third setting value to a larger value, and the CT value changing point from a value larger than the third setting value to a smaller value.

14. An apparatus for cerebral hemorrhage segmentation according to claim 12, wherein:
each of said primary searching means and said secondary searching means is configured to search a region that has the difference of CT value between adjacent two pixels of 5 or less.

15. An apparatus for cerebral hemorrhage segmentation according to claim 12, wherein:
said postprocessing means is configured to compensate using a dilation calculation with respect to each region.

16. An apparatus for cerebral hemorrhage segmentation according to claim 12, wherein:
the first setting value is 245, the second setting value is 30, the third setting value is 190, the fourth setting value is 300, the fifth setting value is 4, the sixth setting value is 100, the seventh setting value is 40, the eighth setting value is 70, the ninth setting value is 0.015, and the tenth setting value is 0.003.

* * * * *